(12) United States Patent
Rewinkel et al.

(10) Patent No.: US 6,642,253 B2
(45) Date of Patent: Nov. 4, 2003

(54) THROMBIN INHIBITORS COMPRISING AN AMINOISOQUINOLINE GROUP

(75) Inventors: Johannes Bernardus Maria Rewinkel, Oss (NL); Cornelis Marius Timmers, Berghem (NL); Paolo Giovanni Martino Conti, Heesch (NL)

(73) Assignee: Akzo Nobel N. V., Arnhem (NL)

( * ) Notice: Subject to any disclaimer, the term of this patent is extended or adjusted under 35 U.S.C. 154(b) by 0 days.

(21) Appl. No.: 10/332,792

(22) PCT Filed: Jul. 9, 2001

(86) PCT No.: PCT/EP01/07887

§ 371 (c)(1),
(2), (4) Date: Apr. 21, 2003

(87) PCT Pub. No.: WO02/04423

PCT Pub. Date: Jan. 17, 2002

(65) Prior Publication Data

US 2003/0166579 A1 Sep. 4, 2003

(30) Foreign Application Priority Data

Jul. 12, 2000 (EP) ............................................ 00202491

(51) Int. Cl.$^7$ ..................... A61K 31/472; C07D 217/22
(52) U.S. Cl. ........................... 514/310; 546/143; 514/19
(58) Field of Search .................... 514/310, 19; 546/143

(56) References Cited

FOREIGN PATENT DOCUMENTS

WO   98/47876   10/1998

*Primary Examiner*—Charranjit S. Aulakh
(74) *Attorney, Agent, or Firm*—Mark M. Milstean

(57) ABSTRACT

The invention relates to a compound having the formula (I)

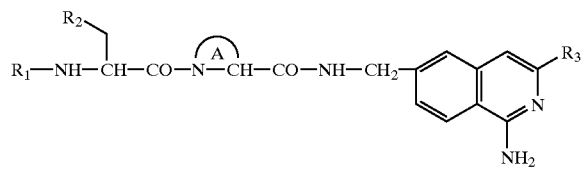

wherein
$R_1$ is cyclopentyl, cyclohexyl or a branched (3–4C)alkyl;
$R_2$ is cyclohexyl or phenyl;
$R_3$ is H or methyl; and
A is an unsubstituted saturated 4, 5 or 6-membered ring; or a pharmaceutically acceptable salt thereof.

The compounds of the invention have anticoagulant activity and can be used in treating or preventing thrombin-mediated and thrombin-associated diseases.

12 Claims, No Drawings

THROMBIN INHIBITORS COMPRISING AN AMINOISOQUINOLINE GROUP

FIELD OF THE INVENTION

The invention relates to a thrombin inhibitor comprising an amnoisoquinoline group, a pharmaceutical composition containing the same, as well as the use of said inhibitor for the manufacture of a medicament for treating and preventing thrombin-related diseases.

BACKGROUND OF THE INVENTION

In literature a large number of peptide-like thrombin inhibitors is disclosed. Most of those thrombin inhibitors contain basic groups at the so-called $P_1$-position, like the basic amino acids arginine and lysine, but also benzamdine and the like. Such a basic moiety is considered essential for antithrombin activity. On the other hand, the basicity of the compounds may impair the uptake of the compounds in the intestines when delivered via the oral route. In WO 98/47876 a class of thrombin inhibitors is disclosed having an aminoisoquinoline moiety as basic group, which show improved trasepithelial transport properties. Within this latter class of compounds a new selection of compounds has now been identified having further improved pharmacological properties.

DETAILED DESCRIPTION OF THE INVENTION

It has now been found that compounds of the formula (I)

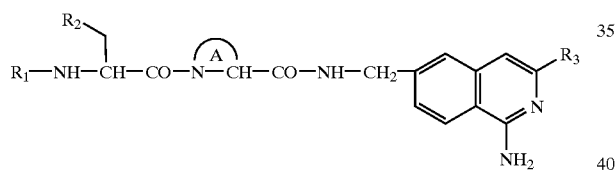

(I)

wherein $R_1$ is cyclopentyl cyclohexyl or a branched (3–4C)alkyl;
$R_2$ is cyclohexyl or phenyl;
$R_3$ is H or methyl; and
A is an unsubstituted saturated 4, 5 or 6-membered ring;
or a pharmaceutically acceptable salt thereof,
are potent thrombin inhibitors having a significantly increased plasma half-life. Most of the clinical situations in which anti-thrombotic drugs are needed require in general a prolonged half-life (see Sixma, J. J. et al., Thromb. Res. 67; 305–311 (esp. 307), 1992). The compounds of this invention thus are an important improvement in the art.

The compounds of the present invention are useful for treating and preventing thrombin-mediated and thrombin-associated diseases. This includes a number of thrombotic and prothrombotic states in which the coagulation cascade is activated which include, but are not limited to, deep vein thrombosis, pulmonary embolism, thrombophlebitis, arterial occlusion from thrombosis or embolism, arterial reocclusion during or after angioplasty or thrombolysis, restenosis following arterial injury or invasive cardiological procedures, postoperative venous thrombosis or embolism, acute or chronic atherosclerosis, stroke, myocardial infarction, cancer and metastasis, and neurodegenerative diseases. The compounds of the invention may also be used as anticoagulants in extracorporeal blood circuits, as necessary in dialysis and surgery. The compounds of the invention may also be used as in vitro anticoagulants.

Preferred thrombin inhibitors according to the invention are compounds wherein A is a five-membered ring. Preferably, $R_2$ is cyclohexyl. Other preferred compounds are those, wherein $R_3$ is H. More preferred are compounds wherein $R_1$ is cyclohexyl. The most preferred thrombin inhibitor according to the invention is the compound wherein $R_1$ is cyclohexyl, $R_2$ is cyclohexyl, $R_3$ is H and A is a five-membered ring.

The term branched (3–4C)alkyl means a branched alkyl group having 3 or 4 carbon atoms, e.g. isopropyl.

The invention further includes a process for the preparation of the thrombin inhibitors, including coupling of suitably protected amino acids and aminoisoquinoline derivatives, followed by removing the protective groups.

The compounds according to the formula (I) may be prepared in a manner conventional for such compounds. They may be prepared by a peptide coupling of compounds of formula (II) with compounds of formula (III) using as a coupling reagent for example N,N-dicyclohexylcarbodiimide (DCCI) and 1-hydroxybenzotriazole (HOBT or 2-(1H-benzotriazol-1-yl)-1,1,3,3-tetramethyluronium tetrafluoroborate (TBTU), wherein $R_1$, $R_2$, $R_3$ and A have the previously defined meanings. The N-terminus of compounds of formula (II) may optionally carry a protective group such as the t-butyloxycarbonyl group (Boc). The aryl amine group of compounds of formula (III) may optionally carry a protective group such as benzoyl which can be removed after the coupling reaction

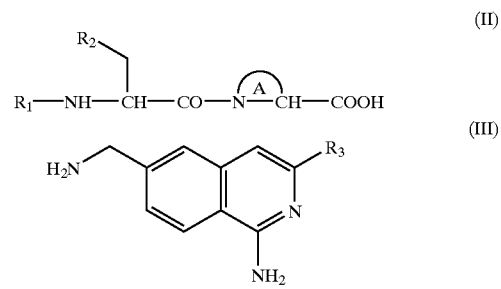

Compounds of formula (II) can be prepared from compounds of formula (IV), wherein Pg1 is a carboxylate protecting group like the benzyl ester, by treatment of compounds of formula (IV) with a appropriate ketone like cyclohexanone or acetone and a reductive agent like sodium triacetoxyborohydride under acidic conditions and thereafter removal of the carboxylate protecting group.

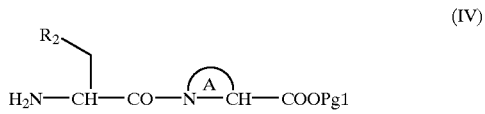

(IV)

The compound of formula (III) wherein $R_3$=H (1-amino-6(aminomethyl)isoquinoline) is described in WO 98/47876. The compound of formula (III) wherein $R_3$=Me (1-amino-6-(aminomethyl)-3-methylisoquinoline) can be prepared from 1-amino-6-methoxy-3-methylisoquinoline using the procedures described in WO 98/47876 for the transformation of 1-amino-6-methoxyisoquinoline into 1-amino-7-(aminomethyl)isoquinoline. 1-Amino-6-methoxy-3-methylisoquinoline can be prepared from 3-methoxyphenylacetone using the method described by W. Zielinski and M. Mazik in Heterocycles 38, 375 (1994).

Alternatively, compounds of formula (I) can be prepared from compounds of formula (V), by treatment of compounds of formula (V) with a appropriate ketone like cyclohexanone or acetone and a reductive agent like sodium triacetoxyborohydride under acidic conditions. In this reaction the aryl amine group of compounds of formula (V) may optionally be protected by a group such as benzoyl which can be removed after the reductive amination.

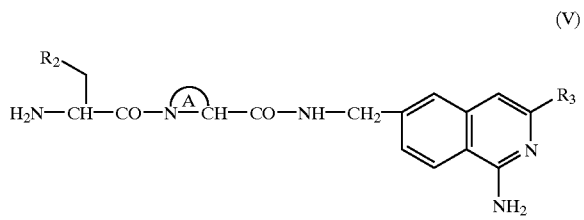

(V)

Compounds of formula (V) can be prepared by a peptide coupling of a dipeptide protected at the N-terminus with a protecting group like the Boc group and compounds of formula (III) using the coupling reagents described before.

Protection of the α-amino functions generally takes place by urethane functions such as the acid-labile tert-butyloxycarbonyl group (Boc), benzyloxycarbonyl (Cbz) group and substituted analogs, the base-labile 9-fluorenylmethyloxycarbonyl (Fmoc) group or the phthaloyl (Phth) group. Other suitable amino protective groups include Nps, Bpoc, Msc, etc. Removal of the protecting groups can take place in different ways, depending on the nature of those protecting groups. Usually deprotection takes place under acidic conditions and in the presence of scavengers. The Cbz group can also be removed by catalytic hydrogenation. An overview of amino protecting groups and methods for their removal is given in The Peptides, Analysis, Synthesis, Biology, Vol. 3 E. Gross and J. Meienhofer, Eds., (Academic Press, New York, 1981).

Protection of carboxyl groups can take place by ester formation e.g. base-labile esters like methyl- or ethylesters, acid labile esters like tert-butylesters, or hydrogenolytically-labile esters like benzylesters.

The compounds of the invention, which may be in the form of a free base, may be isolated from the reaction e in the form of a pharmaceutically acceptable salt. The pharmaceutically acceptable salts may also be obtained by treating the free base of the formula (I) with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, and ascorbic acid.

The compounds of this invention possess one or more chiral carbon atoms, and may therefore be obtained as a pure enantiomer, as a pure diastereomer, as a mixture of enantiomers, or as a mixture containing diastereomers. Methods for obtaining the pure enantiomers are well known in the art, e.g. crystallization of salts which are obtained from optically active acids and the racemic mixture, or chromatography using chiral columns. For diastereomers straight phase or reversed phase columns may be used.

The compounds of the invention may be administered enterally or parenterally, and for humans preferably in a daily dosage of 0.001–100 mg per kg body weight, preferably 0.01–10 mg per kg body weight. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation, or as a spray, e.g. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used.

Suitable carriers with which the compositions can be administered include lactose, starch, cellulose derivatives and the like, or mixtures thereof, used in suitable amounts.

The elimination half-life and percentage bioavailability of the compounds of the invention may suitably be tested according to the following test in dogs.

The residence time and percentage bioavailability of direct thrombin inhibitors in female Beagle dogs may be measured by determination of the anti-IIa activity in plasma after intravenous or oral administration. In view of the selectivity of the protease inhibitors of the invention, inhibition of thrombin linearly relates with the concentration of the measured protease inhibitor. After intravenous or oral administration of the serine protease inhibitor, blood is collected from the jugular vein at different time-points during the day. After centrifugation of the blood, plasma anti-IIa activities are determined of the plasma samples in a microtiter plate chromogenic assay using a calibration curve of the tested compound itself The obtained data are analysed from the plasma vs time curve e.g. by means of a computerised iterative procedure, based on the Simplex method. Subsequently, the elimination half-lives are calculated using the model of relative error independent of the concentration, and the area under the curve (AUC) is determined with the trapezium rule. Assuming linear kinetics, the percentage bioavailability is calculated by dividing the AUC obtained after p.o. administration by the mean expected normalised AUC after i.v. administration of that dose (X100%).

The invention is further illustated by the following examples.

EXAMPLES

The $^1$H NMR measurements were performed on a BRUKER DRX 400 spectrophotometer operating at a $^1$H frequency of 400 MHz. Mass spectra (MS) were recorded with a PE-sciex API-165.

Example 1

N-Cyclohexyl-3-cyclohexyl-D-alanyl-N-[(1-amino-6-isoquinolinyl)methyl]-L-prolinamide Hydrogenchloride (N-Cyclohexyl-D-Cha-Pro-6Aiq.HCl)

After stirring 0.91 g of 3-cyclohexyl-N-[(1,1-dimethylethoxy)carbonyl]-D-alanyl-L-proline phenylmethyl ester (Boc-D-Cha-Pro-OBzl) in 2.5 mL of dichloromethane and 2.5 mL of trifluoroacetic acid at room temperature for two hours the reaction mixture was concentrated in vacuo to yield 0.94 g of an oil. This oil was dissolved in 10 mL of N,N-diethylformamide containing 1% (v/v) acetic acid and 0.26 mL of cyclohexanone and 0.64 g of sodium triacetoxyborohydride were added. After stirring at room temperature for 16 hours 5 mL of water was added to the reaction mixture and extracted with dichloromethane. The organic extract was dried over magnesium sulfate and concentrated to give 0.90 g of an oil (TLC; silica gel, dichloromethane/methanol=95/5 (v/v) Rf=0.8). This oil was dissolved in 50 mL of ethyl acetate, the pH of the solution was adjusted to five using acetic acid, 0.10 g of palladium on carbon (10%) was added and the suspension was hydrogenated at atmospheric pressure at room temperature for one hour. The palladium catalyst was removed by filtration and the solvent was removed by evaporation at reduced pressure. The residue was dissolved in toluene and the toluene was evaporated under reduced pressure yielding 0.56 g of N-cyclohexyl-D-Cha-Pro-OH. This acid (0.35 g) was dissolved in 10 mL of N,N-dimethylformamide and 0.19 mg of 1-amino-6-aminomethylisoquinoline (WO 9847876) and 0.4 g of 2-(1H-benzotriazol-1-yl)-1,1,3,3-tetramethyl uronium tetrafluoroborate (TBTU) were added. The pH of the reaction mixture was adjusted to 8 using N,N-diisopropylethylamine (DIPEA). After stirring for 24 hours at room temperature an additional 0.1 g TBTU was added and the reaction mixture was stirred at room temperature for an additional 18 hours. Thereafter the reaction mixture was concentrated in vacuo. The residue was dissolved in 50 mL of dichloromethane and washed twice with aqueous sodium hydrogencarbonate, dried over magnesium sulfate and concentrated. The residue was dissolved in water and directly charged onto a preparative HPLC DeltaPak RP-$C_{18}$ using a gradient elution system of 20% A/80% B to 20% A/30% B/50% C over 60 min at a flow rate of 40 ml/min (A: 0.5M phosphate buffer pH 2.1, B: water, C: acetonitril/water=6/4 (v/v)). Yield: 0.25 g of the title compound.

$^1$H-NMR 400 MHz (CD$_3$OD) δ: 0.84–2.41 (27H, m), 2.91–3.01 (1H, m), 3.57–3.65 (1H, m), 3.81–3.88 (1H, m), 4.30 (1H, t, J=7 Hz), 4.49–4.77 (3H, m), 7.26 (1H, d, J=7 Hz), 7.57 (1H, d, J=7 Hz), 7.73 (1H, dd, J=2 Hz and J=9 Hz), 7.92 (1H, d, J=2 Hz), 8.38 (1H, d, J=9 Hz).

Example 2

N-Cyclohexyl-3-cyclohexyl-D-alanyl-N-[(1-amino-3-methyl-6-isoquinolinyl)methyl]-L-prolinamide Hydrogenchloride (N-Cyclohexyl-D-Cha-Pro-6(3Me)Aiq.HCl)

2a. 1-Amino-6-methoxy-3-methyl-isoquinoline

A solution of 2.12 g of 3-methoxyphenylacetone and 1.26 mL of phosphoryl chloride in 45 mL of anhydrous toluene was heated under reflux. After 30 minutes the mixture was cooled to 0° C. and a solution of 0.57 g of cyanamide in 23 mL of anhydrous ether was added dropwise. The reaction mixture was allowed to warm to room temperature and stirred at this temperature for one hour. Then the stirred mixture was cooled to 0° C. and 1.5 mL of titanium tetrachloride was added dropwise. The reaction mixture was heated under reflux for 2.5 hours, cooled, 34 mL of water added, the mixture filtered and the sediment was washed with ethyl acetate. The filtrate was made basic using 2N aqueous sodium hydroxide and acted with ethyl acetate. The organic extracts were washed with brine, dried over magnesium sulfate and concentrated. The residue was purified by silica chromatography (dichloromethane/methanol=95/5) yielding 0.42 g of the title compound. $^1$H-NMR 400 MHz (CDCl$_3$) δ: 2.45 (3H, s), 3.91 (3H, s), 5.0 (2H, br. s), 6.81 (1H, s), 6.90 (1H, d, J=3 Hz), 7.02 (1H, dd, J=3 Hz and J=9 Hz), 7.65 (1H, d, J=9 Hz).

2b. 1-Amino-6-hydroxy-3-methyl-isoquinoline

Boron tribomide (4 mL) in 6 mL of dichloromethane was added dropwise to a stirred solution of 1-amino-6-methoxy-3-methylisoquinoline (2 g) in 10 mL of dichloromethane at 0° C. After stirring for 16 hours at ambient temperature the reaction mixture was poured on ice, the organic layer removed and the pH of the aqueous layer adjusted to pH 9 by adding concentrated aqueous ammonia. The precipitated material was collected by filtration and dried in vacuo to give 1.6 g of the title compound. ESI-MS: 175 (MH$^+$).

2c. Trifluoro-methanesulfonic Acid 1-Amino-3-methyl-isoquinolin-6-yl Ester

A mixture of 1.4 g of 1-amino-6-hydroxy-3-methyl-isoquinoline and 4.3 g of N-phenyl-bis(trifluoromethane-sulfonimid) in 19.5 mL of dichloromethane and 19.5 mL of dioxane was cooled in an ice bath and 2.8 mL of N,N-diisopropylethylamine added dropwise. The resulting mixture was heated for 24 h at 70° C., after which the volatiles were removed in vacuo. The remaining residue was dissolved in ethyl acetate, washed with successive portions of 2N aqueous sodium hydroxide, water and brine and dried (sodium sulfate). Filtration and concentration afforded a colourless oil, which was triturated in toluene to give 1.3 g of a solid. The toluene solution was purified by silica chromatography (toluene/ethanol=95/5) yielding an additional 0.6 g of the title compound. Total yield 1.9 g. ESI-MS: 307 (MH$^+$).

2d. 1-Amino-6-cyano-3-methylisoquinoline

Palladium acetate (0.28 g) was added to a heated mixture of trifluoro-methanesulfonic acid 1-amino-3-methylisoquinolin-6-yl ester (1.9 g), zinc cyanide (0.74 g) and triphenylphosphine (0.33 g) in 24 mL of N-methyl-pyrrolidone at 190° C. (exothermic!). Stirring was continued at 190° C. for 2 h After cooling to room temperature, ethyl acetate was added and the organic mixture washed with 2N aqueous ammonia, water and brine and dried (magnesium sulfate). Filtration and concentration afforded a brownish oil, which was purified by silica chromatography (dichloromethane/methanol=98/2) to give 0.68 g of the title compound. ESI-MS: 184 (MH$^+$).

2e. 1-Amino-6-(aminomethyl)-3-methylisoquinoline

To a stirred solution of 1-amino-6-cyano-3-methylisoquinoline (0.68 g) in 15 mL of tetrahydrofuran at room temperature under a nitrogen atmosphere was added 8.4 mL of 2M borane-methylsulfide complex in tetrahydrofuran and thereafter heated at 60° C. for 50 minutes. The reaction mixture was cooled in an ice bath and 7.5 mL of methanol was added slowly. After 15 minutes 18.8 mL of 1M hydrogen chloride in ether was added. The reaction mixture was allowed to warm to room temperature and stirred for an additional 16 hours. The solid was isolated to afford 0.34 g of 1-amino-6-(aminomethyl)-3-methylisoquinoline hydrogenchloride. The filtrate was purified using column chromatography (silica gel; methanol/ammonia=98/2) to yield an additional 0.15 g of 1-amino-6-(aminomethyl)-3-methylisoquinoline. ESI-MS: 188 (MH$^+$).

2f. N-Cyclohexyl-3-cyclohexyl-D-alanyl-N-[(1-amino-3-methyl-6-isoquinolinyl)methyl]-L-prolinamide Hydrogenchloride (N-Cyclohexyl-D-Cha-Pro-6(3Me)Aiq.HCl)

To a stirred mixture of 0.17 g of 1-amino-6-(aminomethyl)-3-methylisoquinoline hydrogenchloride, 0.30 g of N-cyclohexyl-D-Cha-Pro-OH, 0.5 mL of acetonitrile and 0.37 mL of N,N-diisopropylethylamine in 3 mL of N,N-dimethylformamide at room temperature was added in one hour a solution of 0.35 g of bromotripyrrolidonophosphonium hexafluorophosphate (PyBroP) in 1.3 mL of N,N-dimethylformamide. After stirring for 24 hours at room temperature the reaction mixture was concentrated in vacuo. The residue was dissolved in ethyl acetate and washed with aqueous sodium hydrogencarbonate and brine, dried over magnesium sulfate and concentrated. The residue was purified by silica chromatography (dichloromethane/methanol=9/1) and lyophilisation from t-butanol/hydrochloric acid yielded 0.13 g of the title compound. $^1$H-NMR 400 MHz (CD$_3$OD) δ: 0.85–2.40 (27H, m), 2.50 (0.3H, s), 2.51 (2.7H, s), 2.92–3.00 (1H, m), 3.54–3.68 (1H, m), 3.81–3.88 (1H, m), 4.30 (1H, t, J=7 Hz), 4.46–4.74 (3H, m), 7.02 (1H, s), 7.64 (1H, dd, J=2 Hz and J=9 Hz), 7.80 (1H, d, J=2 Hz), 8.32 (1H, d, J=9 Hz).

Example 3

N-Cyclohexyl-D-phenylalanyl-N-[(1-amino-6-isoquinolinyl)methyl]-L-prolinamide Hydrogenchloride (N-Cyclohexyl-D-Phe-Pro-6Aiq.HCl)

Starting with 0.85 g of N-[(1,1-dimethylethoxy)carbonyl]-D-phenylalanyl-L-proline phenylmethyl ester (Boc-D-Phe-Pro-OBzl) gave 0.82 g of N-cyclohexyl-D-phenylalanyl-L-proline (N-cyclohexyl-D-Phe-Pro-OH) using the procedures described in example 1 for N-cyclohexyl-D-Cha-Pro-OH. N-cyclohexyl-D-Phe-Pro-OH (0.82 g) was dissolved in 10 mL of N,N-dimethylformamide and 0.33 mg of 1-amino-6-aminomethylisoquinoline and 1.1 g of O-(7-azabenzotrazol-1-yl)-N,N,N',N'-tetramethyluronium hexafluorophosphate (HATU) were added and the pH was adjusted to 8 using N,N-diisopropylethylamine (DIPEA). After stirring for 16 hours at room temperature the reaction mixture was concentrated in vacuo. The residue was dissolved in 50 mL of dichloromethane and washed twice with water and brine, dried over magnesium sulfate and concentrated. The residue was purified by silica chromatography (dichloromethane/methanol (containing 2% ammonia)=9/1) and lyophilisation from t-butanol/hydrochloric acid yielded 0.19 g of the title compound. $^1$H-NMR 400 MHz (CD$_3$OD) δ: 0.87–2.13 (14H, m), 2.38–2.45 (1H, m), 2.94–3.03 (1H, m), 3.06–3.13 (1H, m), 3.25–3.38 (2H, m), 4.33–4.73 (4H, m), 7.25–7.40 (6H, m), 7.58 (1H, d, J=7 Hz), 7.71 (1H, dd, J=2 Hz and J=9 Hz), 7.92 (1H, d, J=2 Hz), 8.35 (1H, d, J=9 Hz).

Example 4

N-Cyclopentyl-3-cyclohexyl-D-alanyl-N-[(1-amino-6-isoquinolinyl)methyl]-L-prolinamide Hydrogenchloride (N-Cyclopentyl-D-Cha-Pro-6Aiq.HCl)

Using the procedures described in example 1 starting with 0.30 g of Boc-D-Cha-Pro-OBzl using cyclopentanone instead of cyclohexanone gave crude N-cyclopentyl-D-Cha-Pro-6Aiq which was purified using column chromatography (silica gel; dichloromethane/methanol=10/1 gradient to 5/1). Lyophilisation from t-butanol/hydrochloric acid yielded 0.16 g of the title compound. $^1$H-NMR 400 MHz (CD$_3$OD) δ: 0.85–2.41 (25H, m), 3.43–3.52 (1H, m), 3.59–3.65 (1H, m), 3.80–3.86 (1H, m), 4.20 (1H, t, J=7 Hz), 4.51–4.73 (3H, m), 7.25 (1H, d, J=7 Hz), 7.57 (1H, d, J=7 Hz), 7.73 (1H, dd, J=2 Hz and J=9 Hz), 7.90 (1H, d, J=2 Hz), 8.38 (1H, d, J=9 Hz).

Example 5

N-(1-Metylethyl)-3-cyclohexyl-D-alanyl-N-[(1-amino-6-isoquinolinyl)methyl]-L-prolinamide Hydrogenchloride (N-(1-Metylethyl)-D-Cha-Pro-6Aiq.HCl)

Using the procedures described in example 1 starting with 0.92 g of Boc-D-Cha-Pro-OBzl using acetone instead of cyclohexanone gave 0.04 g of N-(1-metylethyl)-D-Cha-Pro-6Aiq.HCl.

$^1$H-NMR 400 MHz (CD$_3$OD) δ: 0.85–2.41 (23H, m), 3.27–3.35 (1H, m), 3.59–3.65 (1H, m), 3.82–3.89 (1H, m), 4.27 (1H, t, J=7 Hz), 4.51–4.74 (3H, m), 7.26 (1H, d, J=7 Hz), 7.57 (1H, d, J=7 Hz), 7.72 (1H, dd, J=2 Hz and J=9 Hz), 7.91 (1H, d, J=2 Hz), 8.38 (1H, d, J=9 Hz).

Anti-thrombin Assay

The anti-thrombin activity of compounds of the present invention was assessed by measuring spectrophotometrically the rate of hydrolysis of the chromogenic substrate s-2238 exterted by thrombin. This assay for anti-thrombin activity in a buffer system was used to assess the IC$_{50}$-value of a test compound.

Test medium: Tromethamine-NaCl-polyethylene glycol 6000 (TNP) buffer

Reference compound: I2581 (Kabi)

Vehicle: TNP buffer. Solubilisation can be assisted with dimethylsulphoxide, methanol, ethanol, acetonitrile or tert.-butyl alcohol which are without adverse effects in concentrations up to 2.5% in the final reaction mixture.

Technique

Reagents* 1. Tromethamine-NaCl (TN) buffer [Composition of the buffer: Tromethamine (Tris) 6.057 g (50 mmol), NaCl 5.844 g (100 mmol), Water to 1 l. The pH of the solution is adjusted to 7.4 at 37° C. with HCl (10 mmol·l$^{-1}$)]; 2. TNP buffer (Polyethylene glycol 6000 is dissolved in TN buffer to give a concentration of 3 g·l$^{-1}$); 3. S-2238 solution [One vial S-2238 (25 mg; Kabi Diagnostica, Sweden) is dissolved in 20 ml TN buffer to give a concentration of 1.25 mg·ml$^{-1}$ (2 mmol·l$^{-1}$)]; 4. Thrombin solution [Human thrombin (16 000 nKat·vial$^{-1}$; Centraal Laboratorium voor Bloedtransfusie, Amsterdam, The Netherlands) is dissolved TNP buffer to give a stock solution of 835 nKat·ml$^{-1}$. Immediately before use this solution is diluted with NP buffer to give a concentration of 3.34 nKat·ml$^{-1}$.]

*All ingredients used are of analytical grade

For aqueous solutions ultrapure water (Mlli-Q quality) is used.

Preparation of Test and Reference Compound Solutions

The test and reference compounds are dissolved in Milli-Q water to give stock concentrations of 10$^{-2}$ mol·l$^{-1}$. Each concentration is stepwise diluted with the vehicle to give concentrations of 10$^{-3}$, 10$^{-4}$ and 10$^{-5}$ mol·l$^{-1}$. The dilutions, including the stock solution, are used in the assay (final concentrations in the reaction mixture: 3·10$^{-3}$; 10$^{-3}$; 3·10$^{-4}$; 10$^{-4}$; 3·10$^{-5}$; 10$^{-5}$; 3·10$^{-6}$ and 10$^{-6}$ mol·l$^{-1}$, respectively).

Procedure

At room temperature 0.075 ml and 0.025 ml test compound or reference compound solutions or vehicle are alternately pipetted into the wells of a microtiter plate and these solutions are diluted with 0.115 ml and 0.0165 ml TNP buffer, respectively. An aliquot of 0.030 ml S-2238 solution is added to each well and the plate is pre-heated and pre-incubated with shaking in an incubator (Amersham) for 10 min. at 37° C. Following pre-incubation the hydrolysis of S-2238 is started by addition of 0.030 ml thrombin solution to each well. The plate is incubated (with shaking for 30 s) at 37° C. Starting after 1 min of incubation, the absorbance of each sample at 405 nm is measured every 2 min. for a period of 90 min. using a kinetic microtiter plate reader (Twinreader plus, Flow Laboratories).

All data are collected in an IBM personal computer using LOTUS-MEASURE. For each compound concentration (expressed in mol·l$^{-1}$ reaction mixture) and for the blank the absorbance is plotted versus the reaction time in min.

Evaluation of responses: For each final concentration the maximum absorbance was calculated from the assay plot.

The $IC_{50}$-value (final concentration, expressed in $\mu mol \cdot l^{-1}$, causing 50% inhibition of the maximum absorbance of the blank) was calculated using the logit transformation analysis according to Hafner et al. (Arzneim.-Forsch./Drug Res. 1977; 27(II): 1871–3).

| Antithrombin activity: | |
|---|---|
| Example | $IC_{50}$ (mol · $l^{-1}$) |
| 1 | 0.03 |
| 2 | 0.14 |
| 3 | 0.13 |
| 4 | 0.12 |
| 5 | 0.29 |

We claim:

1. A compound having the formula (I)

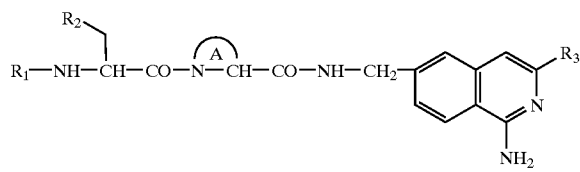

(I)

wherein $R_1$ is cyclopentyl, cyclohexyl or a branched (3–4C)alkyl;

$R_2$ is cyclohexyl or phenyl;

$R_3$ is H or methyl; and

A is an unsubstited saturated 4, 5 or 6-membered ring;

or a pharmaceutically acceptable salt thereof.

2. The compound of claim 1, wherein A is a five-membered ring.

3. The compound of claim 1, wherein $R_2$ is cyclohexyl.

4. The compound of claim 1, wherein $R_3$ is H.

5. The compound of claim 1, wherein $R_1$ is cyclohexyl.

6. The compound of claim 5, wherein $R_1$ is cyclohexyl, $R_2$ is cyclohexyl $R_3$ is H and A is a five-membered ring.

7. A pharmaceutical composition, comprising:

the compound according to claim 1, and pharmaceutically suitable auxiliaries.

8. A method of treating a thrombin-related disease in a patient in need thereof, comprising:

administering an effective amount to treat a thrombosis-related disease in a patient in need thereof the compound according to claim 1.

9. The method according to claim 8, wherein the thrombin-related disease is deep vein thrombosis; pulmonary embolism; thrombophlebitis; arterial occlusion from thrombosis or embolism; arterial reocclusion during or after angioplasty or thrombolysis; restenosis following arterial injury or invasive cardiological procedures; postoperative venous thrombosis or embolism; acute or chronic atherosclerosis; stroke; myocardial infarction; cancer and metastasis; or neurodegenerative disease.

10. An anticoagulant in extracorporeal circuits, comprising:

the compound according to claim 1.

11. The anticoagulant according to claim 10, wherein the extracorporeal circuits are a component of a dialysis procedure or a surgical procedure.

12. An in vitro anticoagulant, comprising:

the compound according to claim 1.